(12) United States Patent
Janowitz

(10) Patent No.: US 6,409,292 B1
(45) Date of Patent: Jun. 25, 2002

(54) STORAGE CUPBOARD, IN PARTICULAR FOR HOSPITAL REQUIREMENTS

(75) Inventor: Bernd Janowitz, Wildeshausen (DE)

(73) Assignee: JANOMED Produktions- und Vertriebs, Wildeshausen (DE)

( * ) Notice: Subject to any disclaimer, the term of this patent is extended or adjusted under 35 U.S.C. 154(b) by 0 days.

(21) Appl. No.: 09/495,735

(22) Filed: Feb. 1, 2000

(30) Foreign Application Priority Data

Feb. 3, 1999 (DE) .......................................... 199 04 247

(51) Int. Cl.[7] .............................................. A47B 47/00
(52) U.S. Cl. .................... 312/257.1; 312/350; 312/351; 312/334.1
(58) Field of Search .......................... 312/334.1, 330.1, 312/350, 351, 209, 263, 257.1, 334.4, 334.7

(56) References Cited

U.S. PATENT DOCUMENTS

| | | | | |
|---|---|---|---|---|
| 1,800,052 A | * | 4/1931 | Brumbaugh ............ 312/350 X |
| 2,815,649 A | * | 12/1957 | Di Angelus et al. .... 312/351 X |
| 3,261,585 A | * | 7/1966 | Constantini et al. .... 312/351 X |
| 3,572,874 A | * | 3/1971 | Hassel ................ 312/257.1 |
| 3,856,374 A | * | 12/1974 | Christen ................ 312/263 |
| 4,681,381 A | * | 7/1987 | Sevey .................... 312/350 X |
| 4,882,116 A | | 11/1989 | McMillen et al. |
| 5,031,974 A | * | 7/1991 | Feucht et al. ............... 312/263 |
| 5,069,466 A | * | 12/1991 | Propst ..................... 312/350 X |
| 5,472,270 A | * | 12/1995 | Czarnecky et al. .. 312/330.1 X |
| 5,785,401 A | * | 7/1998 | Bowyer et al. ....... 312/330.1 X |
| 5,913,584 A | * | 6/1999 | Swindell et al. ............ 312/408 |
| 5,927,838 A | * | 7/1999 | Hellman, Jr. ........... 312/263 X |

FOREIGN PATENT DOCUMENTS

| | | |
|---|---|---|
| DE | 1 924 537 | 9/1965 |
| DE | 88 02 388.5 | 7/1988 |
| DE | 92 15 904.4 | 5/1993 |
| DE | 94 01 876.6 | 6/1994 |

OTHER PUBLICATIONS

European Search Report for 2000 EP–0101474, May/2000, 3 pages.

* cited by examiner

Primary Examiner—James O. Hansen
(74) Attorney, Agent, or Firm—Merchant & Gould P.C.

(57) ABSTRACT

A storage cupboard for storing hospital supplies. The storage cupboard comprises a sidewall and perforated rails mounted on the sidewall. Each of the perforated rails defines a plurality of holes. A support wall has oppositely sides, guides for supporting insertable containers on one side, and snap-in toes on the oppositely disposed side. The snap-in toes are adapted for insertion into the holes defined on the perforated rail.".

6 Claims, 6 Drawing Sheets

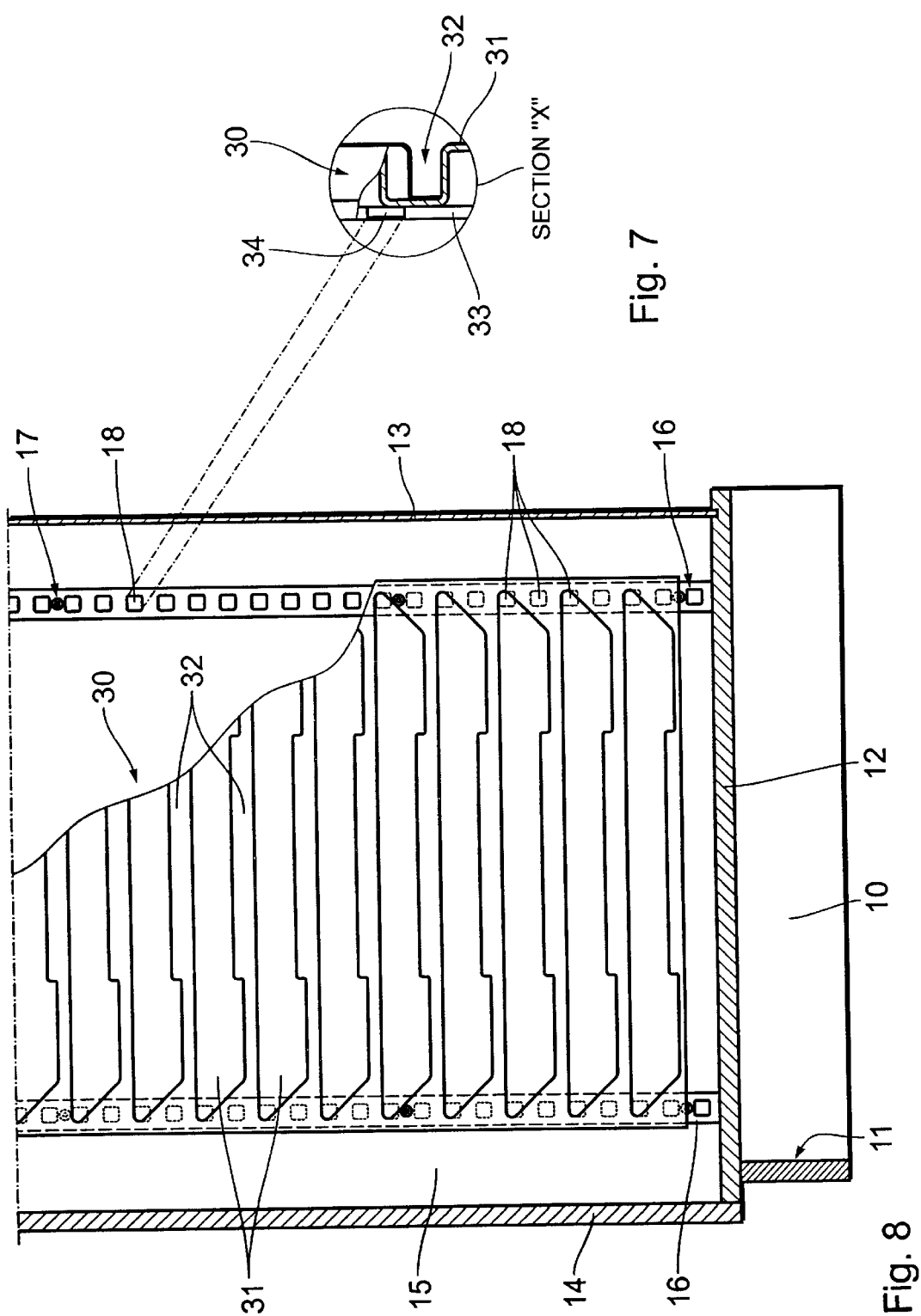

STORAGE CUPBOARD, IN PARTICULAR FOR HOSPITAL REQUIREMENTS

TECHNICAL FIELD

The invention relates to a storage cupboard, in particular for hospital requirements (medicaments, consumable materials such as dressings, etc.), with perforated rails mounted to the two side walls, said perforated rails having a row of holes for snap-on and separable fastening of telescopic rails for extractable drawers.

BACKGROUND

Various systems are known for subdividing the space inside storage cupboards. For the storage and provision of items required in hospitals, a distinction is made between medicaments, on the one hand, and other consumable materials, on the other, whereby the latter particularly include dressings, swabs, cleaning materials etc. For safety reasons, medicaments are supplied in sealed containers and unpacked into stationary drawers in the storage cupboard, whereby said drawers may be extracted by means of telescopic rails. In the case of other, consumable materials, in contrast, the procedure is that containers with drawer—like guide elements on their side, which can be pushed into corresponding guide rails in the storage cupboard, are taken for refilling from the storage cupboard to the central supply depot of the hospital, where they are refilled, then brought back to the storage cupboard and pushed into the respective lateral guide rails of the cupboard.

In the prior art, these lateral guide rails are part of support walls that are fastened by screws on the inside of the side walls, as are the perforated rails for the telescope mounts for stationary drawers. The subdivision of the interior space of such storage cupboards is therefore confined to stationary drawers, on the one hand, and removeable containers, on the other. In practice, however, changes occur in the proportionate amount of storage space required for each of the two storage systems, for example because the relevant hospital ward is assigned to a different department (surgery instead of inner medicine, etc.).

The object of the present invention is to provide a flexible storage cupboard system in which the subdivision of the cupboard interior for the two types of storage can be modified without substantial effort.

SUMMARY

In order to achieve this purpose, the invention proceeds from a solvable arrangement of (horizontal) telescopic drawer rails, such as that described at the outset and known from DE 88 02 388 U1 and 94 01 876 U1, for example, which rails are mounted on {vertically disposed} perforated rails. The invention is characterized by support walls that have guides on the front side for insertable containers, and snap-in toes on the rear side for clipping onto the perforated rails (now freed of telescopic rails). According to the invention, therefore, all side walls have perforated rails on the inside and are fitted according to requirements, either with telescopic rails for drawers or support walls for removeable containers, whereby the former are snapped into the perforated rails in the known manner, and the latter are clipped onto the same perforated rails in a novel way. By combining the attachment of support walls with perforated rails for the telescopic rails, not only do said perforated rails acquire a second use and the desired flexibility is achieved, but a crucially different type of fastening design is provided than that known of an extendable box from DE 92 15 904 U1.

The holes in the perforated rails and the snap-in toes of the support walls are preferably of generally quadratic shape. When fitted with telescopic rails, this permits same to be clipped on by means of punched out portions bent at a right angle that have linear attachment surfaces for engaging with the holes in the perforated rails.

The snap-in toes are comprised advantageously of recesses in the support wall, which is formed of a plastic plate. Thus, they can be easily manufactured when drawing or pressing the support wall support wall to mold the container guides. A particularly firm connection between the support wall and the perforated rails results is obtained when, in a development of the invention, the snap-in toes are of such conical shape that there is tight frictional engagement with the inside edges of the holes in the perforated rails when the support wall is placed onto the perforated rails.

DESCRIPTION OF THE DRAWINGS

The drawing illustrates an embodiment of the invention, whereby:

FIG. 7 is section "X" in FIG. 6 (but on a larger scale);

FIG. 8 is a plan view of the attached support wall in FIG. 6 (partly broken away) and FIG. 9 is a plan view of the fittings on a storage cupboard side wall embodying the present invention, partly with a support wall for guiding removable containers and partly with snap-in telescopic rails for extractable mounting of drawers.

DETAILED DESCRIPTION

Figure 1:
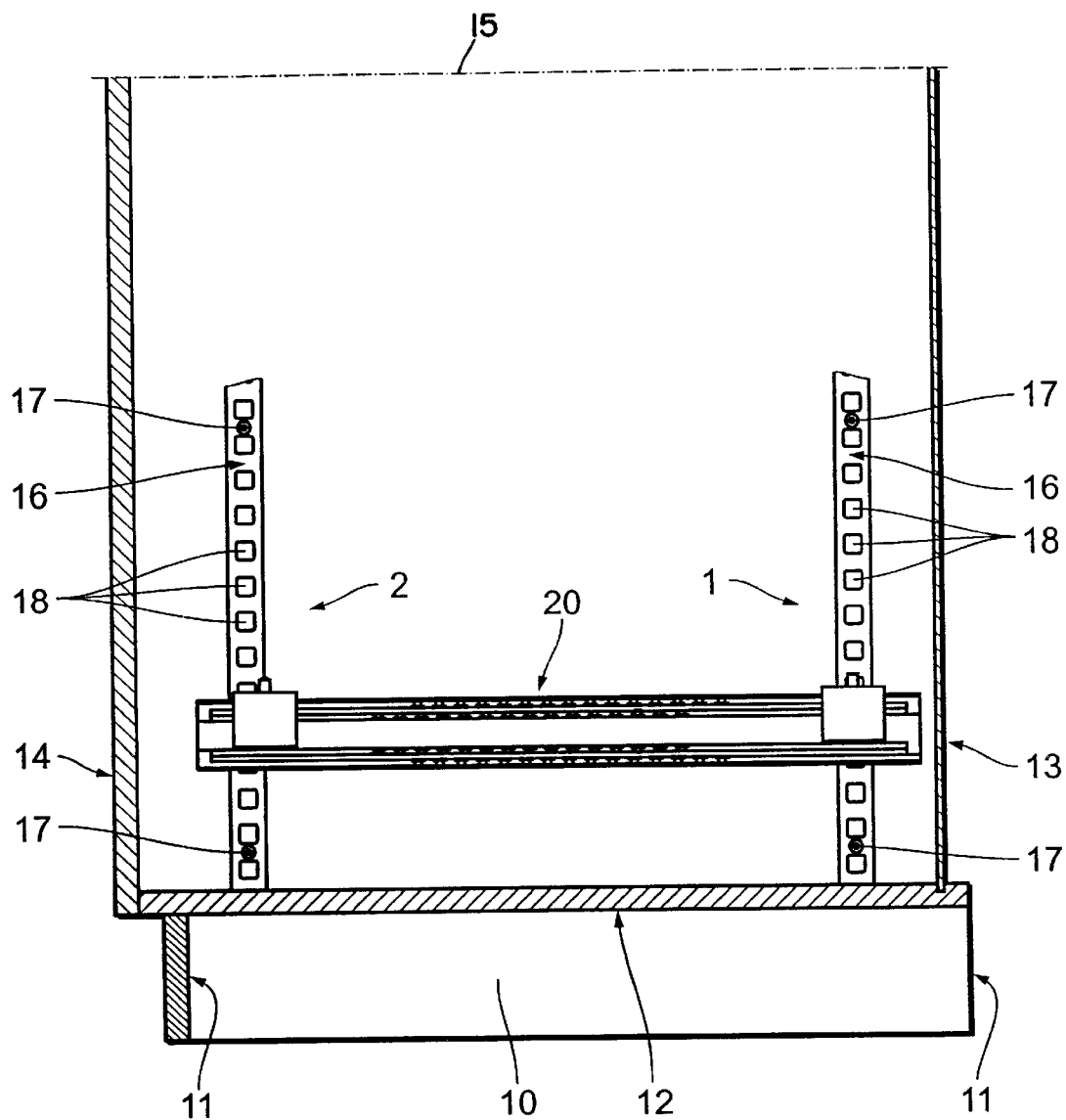
FIG. 1 is a partial longitudinal section of a storage cupboard in the prior art and thus a plan view of its side wall.
Figure 2:
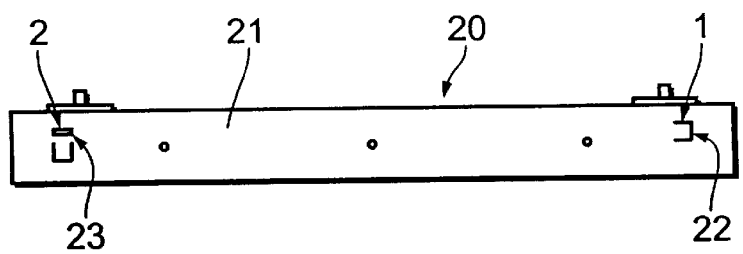
FIG. 2 is a rear view of the telescopic rails latched into perforated rails pursuant to FIG. 1.
Figure 3:
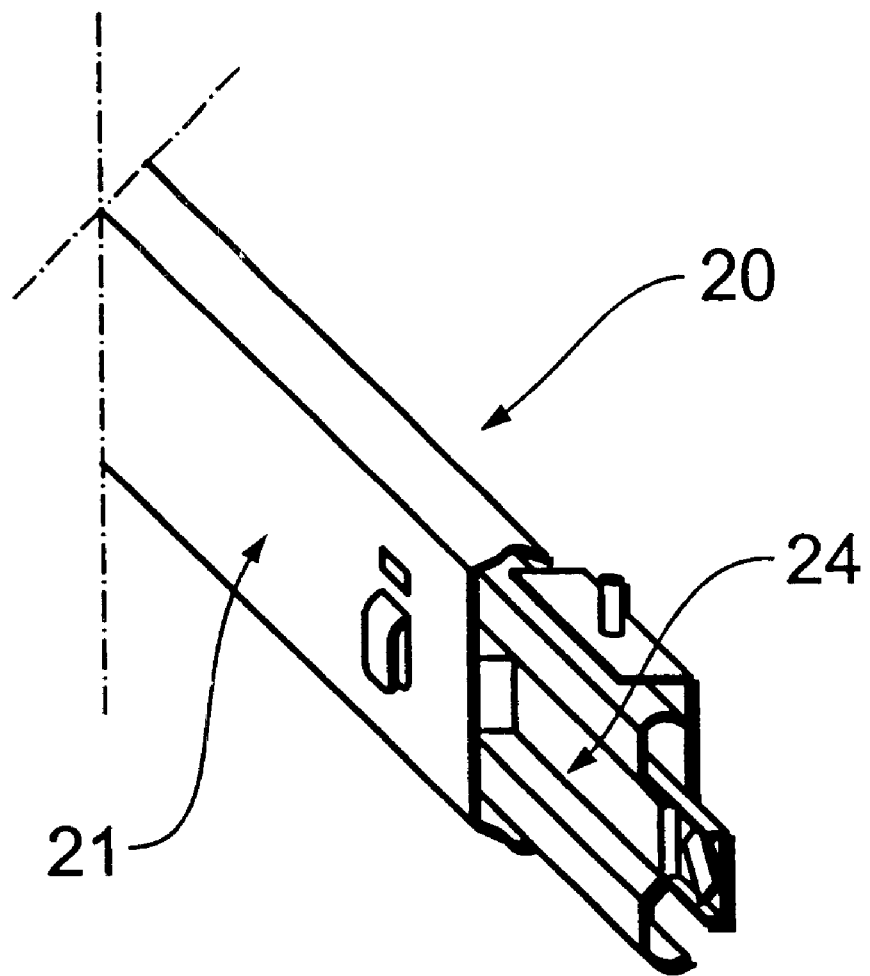
FIG. 3 is a partial perspective view of the telescopic rails pursuant to FIG. 1.
Figure 5:
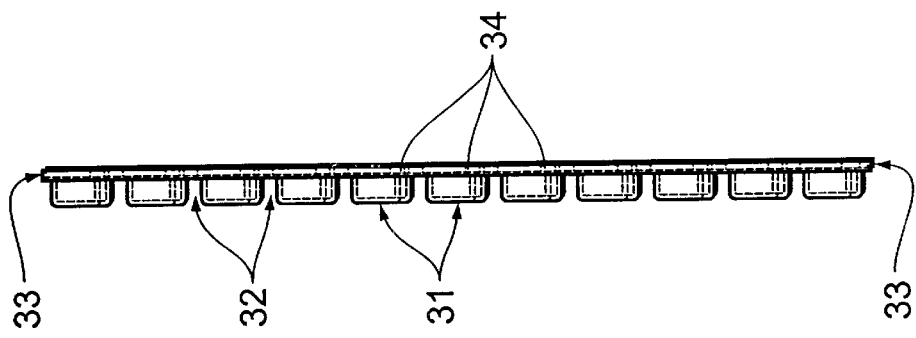
FIG. 5 is a side view of the support wall in FIG. 4.

The storage cupboard shown in partially longitudinal or axial section in FIG. 1 has a base 10 with front base panel 11, a floor 12, a rear wall 13 and a snap-action door 14. Of the two side walls extending between the rear wall 13 and door 14, one side wall 15 is visible in plan view. Vertical perforated rails 16 are mounted on the latter side wall—at the front and rear—by means of screws 17. The perforated rails 16 have a flat O-shaped cross-section of the known type, such that their raised portion, visible in FIG. 1, is at a distance from the inside surface of side wall 15. In a similarly known manner, a series of holes 18 is punched into said raised bar of perforated rail 16, said holes being equidistant from each other and having a quadratic shape in the case illustrated.

Telescopic rails, referred to collectively as 20, can be fastened to perforated rails 16 (only one such rail is shown in FIG. 1) by virtue of its support profile 21 being provided with hooks 22 and 23, which are punched out and bent to a right angle. In the manner known from DE 88 02 388 U1, hook 22, which is open to the rear, is inserted into a hole 18 in the rear perforated rail 16 (adjacent to rear wall 13), whereupon hook 23, which is open to the bottom, can be inserted into the corresponding hole 18 in the front perforated rail 16. Support profile 21 is thus mounted on side wall 15 mounted, and a drawer—not shown—can be attached to the extractable profile 24 of the telescopic rail 20. Up to this point, the system falls under the prior art.

Figure 4:
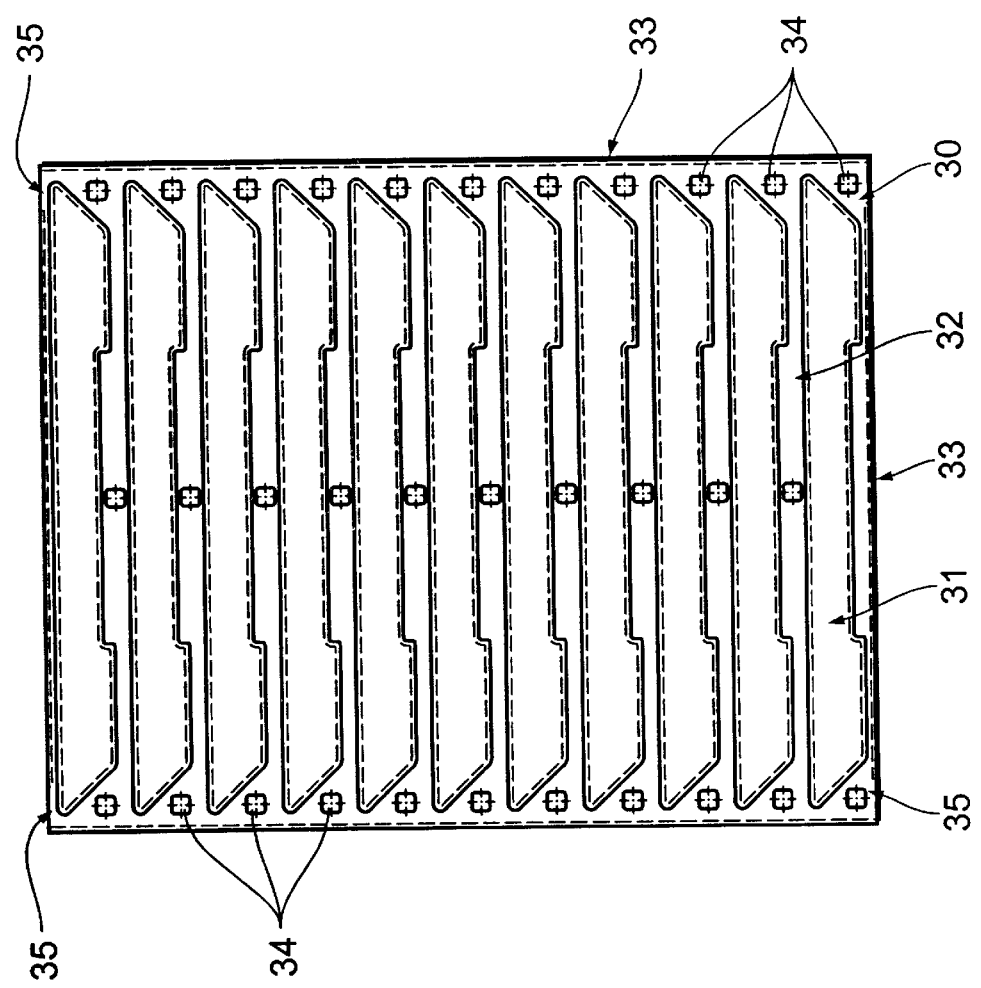
FIG. 4 is a plan view of a support wall (with guides for removable containers) embodying the present invention.

FIG. 4 shown in plan view a support wall 30, the basic design of which is similarly known from the prior art. Said support wall comprises a plastic plate with generally trapezoidally shaped projections 31, between which guide rails 32 are formed for displaceable guiding of extractable containers (not shown). Edge 33 of support wall 30 is bent at right angles around the entire periphery.

Figure 6:
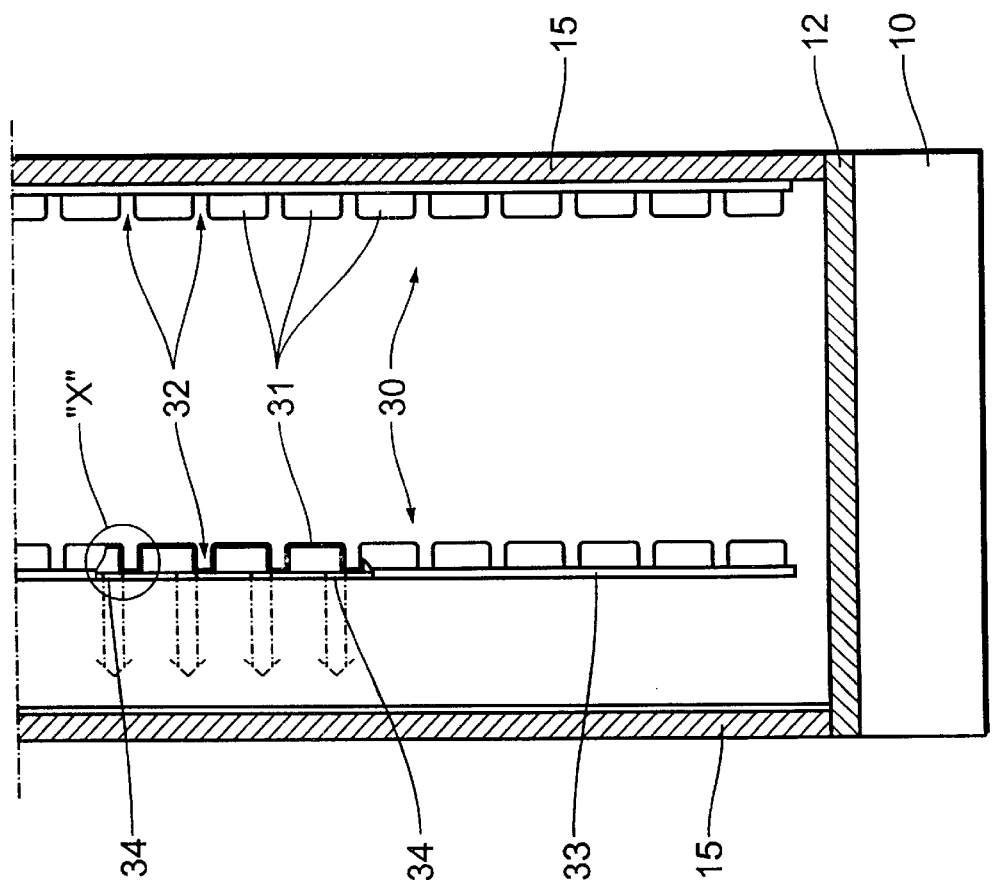
FIG. 6 is a partial cross-sectional view of a storage cupboard embodying the present invention having one attached support wall and one support wall prior to attachment.

From the base level of the (plastic) plate forming support wall 30, which is identical to the base level of guide rails 32, recesses 34 are formed in accordance with the invention corresponding to projections 31 of the opposite side, the form and arrangement of said recesses being shown in particular in the enlarged view of section "X" (from FIG. 6) in FIG. 7. FIGS. 6 and 8—the latter in combination with FIG. 7—illustrate how support wall 30 can be mounted on the perforated rails 16 by inserting the slightly conical recesses 34 into the perforated holes 18. In order that right-angled edge 33 allows the slightly raised perforated rails 16 to pass through, recesses 35 are provided in said edge 33.

Figure 9:
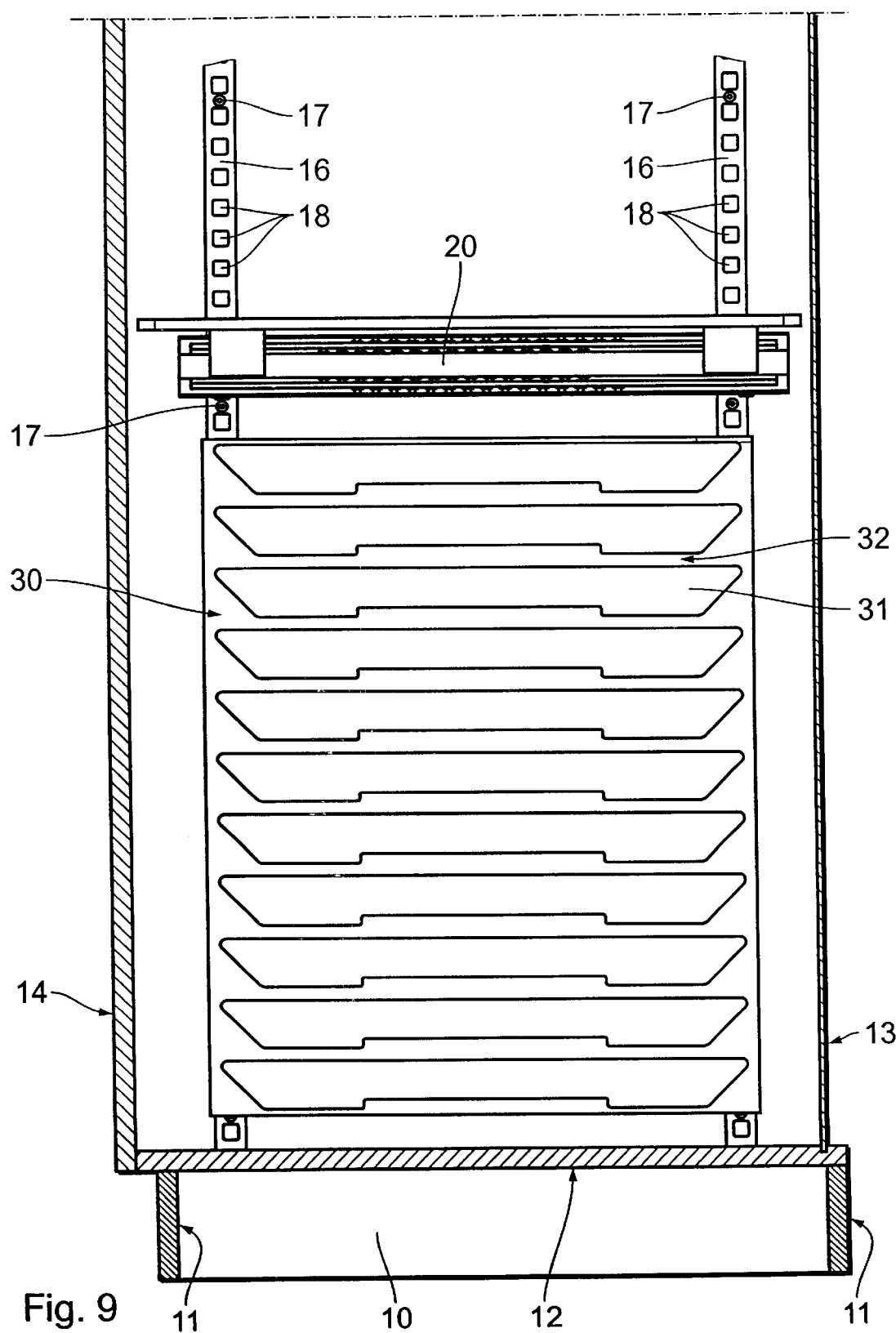

FIG. 9 shows clearly that it is also possible to equip not only adjacently disposed spaces of a storage cupboard in different ways, but also to fit the vertical extent of one and the same cupboard with appropriately configured support walls so that drawers having telescopic rails as well as removeable containers are possible.

What is claimed is:

1. A storage cupboard for storing hospital supplies, the storage cupboard comprising:

a sidewall;

perforated rails mounted on the sidewall, each of the perforated rails defining a plurality of holes;

a support wall having oppositely disposed sides, the support wall having guides for supporting insertable containers on one side and snap-in toes on the oppositely disposed side, the snap-in toes removably inserted into the holes defined on at least one of the perforated rails, without tools or hardware thereby removably securing the support wall to the sidewall; and a telescopic rail wherein the telescopic rail is adapted to support a drawer and has a member adapted to be received by the holes defined in the perforated rail, the telescopic rail being selectively interchangeable with at least one of the support walls.

2. The storage cupboard of claim 1 wherein the holes defined in the perforated rail have a generally rectangular shape and the snap-in toes have a generally rectangular shape.

3. The storage cupboard of claim 2 wherein the snap-in toes are formed by protuberances defined in the support wall.

4. The storage cupboard of claim 1 wherein the snap-in toes have a generally conical shape.

5. The storage cupboard of claim 4 wherein the snap-in toes are formed by protuberances defined in the support wall.

6. A cupboard kit for storing hospital supplies, the kit having selectively interchangeable support walls for supporting an insertable container and telescopic rails for supporting a drawer, the kit comprising:

a cupboard having a sidewall and perforated rails mounted on the sidewall, each of the perforated rails defining a plurality of holes;

two or more support walls, each support wall having oppositely disposed sides, each support wall having guides for supporting insertable containers on one side and snap-in toes on the oppositely disposed side, the snap-in toes removably inserted into the holes defined on the perforated rail, without tools or hardware thereby removably securing the support wall to the sidewall; and two or more telescopic rails, each telescopic rail adapted to support a drawer, and each telescopic rail adapted to be received by the holes defined in at least one of the perforated rails.

* * * * *